US011779609B2

(12) United States Patent
Ito et al.

(10) Patent No.: US 11,779,609 B2
(45) Date of Patent: Oct. 10, 2023

(54) NOTOCHORDAL CELL MATRIX AS A BIOACTIVE LUBRICANT FOR THE OSTEOARTHRITIC JOINT

(71) Applicant: TECHNISCHE UNIVERSITEIT EINDHOVEN, Eindhoven (NL)

(72) Inventors: Keita Ito, Eindhoven (NL); Stefan Antonius Henricus De Vries, Eindhoven (NL)

(73) Assignee: TECHNISCHE UNIVERSITEIT EINDHOVEN, Eindhoven (NL)

( * ) Notice: Subject to any disclaimer, the term of this patent is extended or adjusted under 35 U.S.C. 154(b) by 468 days.

(21) Appl. No.: 16/965,046

(22) PCT Filed: Jan. 30, 2019

(86) PCT No.: PCT/EP2019/052304
§ 371 (c)(1),
(2) Date: Jul. 27, 2020

(87) PCT Pub. No.: WO2019/149787
PCT Pub. Date: Aug. 8, 2019

(65) Prior Publication Data
US 2021/0113626 A1    Apr. 22, 2021

Related U.S. Application Data

(60) Provisional application No. 62/623,672, filed on Jan. 30, 2018.

(51) Int. Cl.
*A61P 19/02* (2006.01)
*A61P 29/00* (2006.01)
*A61L 27/36* (2006.01)
*A61K 35/30* (2015.01)

(52) U.S. Cl.
CPC .......... *A61K 35/30* (2013.01); *A61L 27/3608* (2013.01); *A61L 27/3687* (2013.01); *A61L 27/3691* (2013.01); *A61P 19/02* (2018.01); *A61P 29/00* (2018.01); *A61L 2430/40* (2013.01)

(58) Field of Classification Search
CPC ........ A61K 35/30; A61K 35/32; A61K 35/12; A61L 27/3608; A61L 27/3687; A61L 27/3691; A61L 2430/40; A61P 19/02; A61P 29/00
See application file for complete search history.

(56) References Cited

U.S. PATENT DOCUMENTS

| 6,723,335 | B1 | 4/2004 | Moehlenbruck et al. |
| 2009/0202653 | A1 | 8/2009 | Erwin et al. |
| 2012/0045419 | A1* | 2/2012 | Erwin et al. ......... C12N 5/0655 424/93.7 |
| 2016/0015753 | A1 | 1/2016 | Temple |
| 2016/0235892 | A1 | 8/2016 | Detamore et al. |
| 2019/0022145 | A1 | 1/2019 | O'Heeron |
| 2019/0022278 | A1 | 1/2019 | Ito et al. |

FOREIGN PATENT DOCUMENTS

| WO | 02/081660 A1 | 10/2002 | |
| WO | 2015/048317 A1 | 4/2015 | |
| WO | WO2015048317 A1 * | 4/2015 | ............. A61L 27/54 |
| WO | 2017/121736 A1 | 7/2017 | |
| WO | 2017/123951 A1 | 7/2017 | |
| WO | WO2017123951 A1 * | 7/2017 | |

OTHER PUBLICATIONS

Kwon, JS et al.: "Injectable Extracellular Matrix Hydrogel Developed Using Porcine Articular Cartilage.", International Journal of Pharmaceutics., vol. 454, No. 1, Sep. 15, 2013 (Sep. 15, 2013) (Year: 2013).*
May 9, 2019 International Search Report issued in International Patent Application No. PCT/EP2019/052304.
May 9, 2019 Written Opinion issued in International Patent Application No. PCT/EP2019/052304.
Mar. 28, 2022 Office Action issued in U.S. Appl. No. 16/068,752.
Apr. 1, 2021 Office Action issued in U.S. Appl. No. 16/261,771.
Sep. 15, 2021 Office Action issue in U.S. Appl. No. 16/261,771.
Oct. 27, 2020 Office Action issued in U.S. Appl. No. 16/068,752.
Sep. 15, 2021 Office Action issued in U.S. Appl. No. 16/068,752.
May 25, 2021 Office Action issued in U.S. Appl. No. 16/068,752.
Risbud et al.; "Notochordal Cells in the Adult Intervertebral Disc: New Perspective on an Old Question." Critical Reviews in Eukaryotic Gene Expression; 2011; vol. 21; No. 1; pp. 29-41.
Liu et al.; "CD24 identifies nucleus pulposus progenitors/notochordal cells for disc regeneration." Journal of Biological Engineering; 2018; vol. 12; No. 35; pp. 1-15.
Illien-Jünger et al.; "Development of a Bovine Decellularized Extracellular Matrix-Biomaterial for Nucleus Pulposus Regeneration"; Journal of Orthopaedic Research; 2016; vol. 34; No. 5; pp. 876-888.
Apr. 6, 2017 International Search Report issued in International Patent Application No. PCT/EP2017/050431.
Apr. 6, 2017 Written Opinion issued in International Patent Application No. PCT/EP2017/050431.
Yuan et al.; "Effects of nucleus pulposus cell-derived acellular matrix on the differentiation of mesenchymal stem cells"; Biomaterials; 2013; vol. 34; pp. 3948-3961.
Mercuri et al.; "Novel tissue-derived biomimetic scaffold for regenerating the human nucleus pulposus"; Journal of Biomedical Materials Research A; 2011; vol. 96. No 2; pp. 422-435.

(Continued)

*Primary Examiner* — Jeremy C Flinders
*Assistant Examiner* — Thomas R. Amick
(74) *Attorney, Agent, or Firm* — Oliff PLC

(57) ABSTRACT

A notochordal cell matrix solution as a bioactive lubricant in the treatment of Osteoarthritis, more specifically for use as a bioactive lubricant in viscosupplementation. The notochordal cell matrix solution is capable of reducing the pain in osteoarthritic joints.

Figure 1:
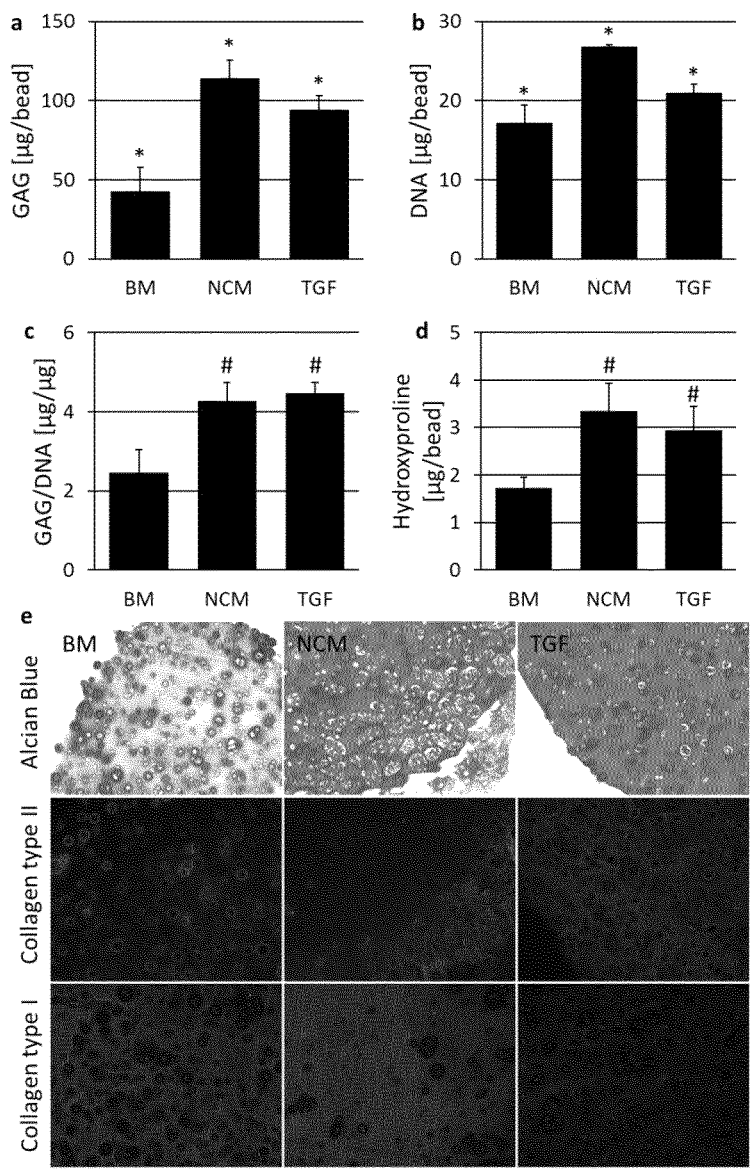

20 Claims, 5 Drawing Sheets
Specification includes a Sequence Listing.

(56) References Cited

OTHER PUBLICATIONS

Wachs et al.; "Creation of an injectable in situ gelling native extracellular matrix for nucleus pulposus tissue engineering"; The Spine Journal; 2016; pp. 1-10.
Liu et al.; "Modulating Notochordal Differentiation of Human Induced Pluripotent Stem Cells Using Natural Nucleus Pulposus Tissue Matrix"; PLOS One; 2014; vol. 9; No. 7; e100885, 8 pages.
U.S. Appl. No. 16/261,771, filed Jan. 30, 2019 in the name of Keita Ito et al.
U.S. Appl. No. 16/068,752, filed Jul. 9, 2018 in the name of Keita Ito et al.
Dec. 8, 2022 Office Action issued in Japanese Patent Application No. 2020-540742.
De Vries, S.A.H et al. "Notochordal Cell Matrix as a Bioactive Lubricant for the Osteoarthritic Joint," Scientific Reports, vol. 8, Article 8875, Jun. 2018, pp. 1-11.

\* cited by examiner

NOTOCHORDAL CELL MATRIX AS A BIOACTIVE LUBRICANT FOR THE OSTEOARTHRITIC JOINT

FIELD OF THE INVENTION

This invention relates to methods and uses of a notochordal cell matrix as a bioactive lubricant in the treatment of oesteoarthritis.

SUMMARY OF THE INVENTION

In the field of intervertebral disc (IVD) regeneration, notochordal cells (NCs) have received considerable attention. They produce soluble factors capable of stimulating nucleus pulposus cell (NPC) matrix production and proliferation[12-15] as well as differentiation of bone marrow-derived stem cells (BMSCs) to a chondrogenic phenotype[16,17]. An alternative to NC-secreted factors is the direct use of lyophilized and pulverized porcine NC matrix (NCM). This material was applied in an in vitro culture of bovine NPCs (de Vries, Stefan; van D, MeijBjörn; Tryfonidou, Marianna; Ito, Keita. Notochordal Cell Matrix As a Therapeutic Agent for Intervertebral Disc Regeneration. Tissue Engineering Part A. June 2018: ten.tea.2018.0026.), where it exerted an even stronger anabolic effect compared to NC-secreted soluble factors. Moreover, intradiscal injection of NCM in a canine in vivo study had anabolic and anti-inflammatory effects and increased IVD hydration (Bach F C, Tellegen A R, Beukers M, et al. Biologic canine and human intervertebral disc repair by notochordal cell-derived matrix: from bench towards bedside. Oncotarget. 2018; 9(41):26507-26526). Since NPCs closely resemble articular chondrocytes, NCM may also have the potential to stimulate these cells. Moreover, when dissolved at a low concentration in aqueous media, NCM forms a viscous fluid that may have lubricating properties, similar to HA.

Notochordal cell matrix (NCM) has regenerative potential on nucleus pulposus cells of the intervertebral disc in vitro and in vivo. It has also been demonstrated that NCs secrete factors with anabolic and anti-inflammatory potential on human chondrocytes. Moreover, when dissolved at a low concentration, NCM forms a viscous fluid that may have lubricating properties. Therefore, this invention describes a novel approach to use NCM as a regenerative lubricant for application in the osteoarthritic (OA) joint. Bovine chondrocyte-seeded alginate beads were cultured in medium supplemented with NCM to test NCM's regenerative potential. In addition, alginate beads were also cultured in NCM stimulated with IL-1β, to investigate NCM's effects in an inflammatory environment. Lastly, reciprocating sliding friction tests of cartilage on glass were performed to test NCM's lubricating properties relative to and in combination with hyaluronic acid (HA). NCM increased GAG deposition and cell proliferation, as well as GAG per DNA ratio and hydroxyproline content. These effects were maintained in the presence of IL-1β. NCM also mitigated expression of IL-1β-induced IL-6, IL-8, ADAMTS-5 and MMP-13. Furthermore, NCM induced a dose-dependent reduction of the coefficient of friction (CoF) similar to HA at a test speed of 6, as well as 60 mm/s. The results from this invention indicate that NCM has anabolic and anti-inflammatory effects on chondrocytes, as well as favorable lubricating properties. Therefore, intra-articular NCM injection may have potential as a treatment to minimize pain while restoring the affected cartilage tissue in the OA joint, and warrants further investigation.

DETAILED DESCRIPTION OF THE INVENTION

Articular cartilage (AC) is a layer of smooth hydrated tissue that covers the articulating surfaces of bones in fluid filled synovial joints. Together with the synovial fluid, it provides low friction in these joints during motion. Osteoarthritis (OA), a degenerative joint disease, affects the AC as well as the synovium and subchondral bone, leading to painful articulating dysfunction. Knee OA is one of the leading causes for pain and disability worldwide, with estimates suggesting 9.3 million affected people in the US alone1.

OA is initially treated conservatively, with exercise and pain medication. In later stages, non-steroidal anti-inflammatory drugs or intra-articular steroid injections are prescribed(2). Another treatment option is viscosupplementation(3) i.e. intra-articular injection of hyaluronic acid (HA), a large polysaccharide that is naturally found in synovial fluid (4). HA increases the viscosity(5) of the synovial fluid in addition to providing viscoelasticity thereby contributing to hydrodynamic lubrication of the joint (6, 7). Furthermore, due to molecular interactions at the cartilage surface, it contributes to boundary lubrication as well(8). With OA, HA degrades resulting in a decreased concentration and low molecular weight fragments, which affects the lubricating properties of synovial fluid(9). Injection of HA into the joint aims to increase synovial fluid viscosity and minimize pain to postpone total knee replacement. Although meta-analyses provide contradicting results regarding the efficacy of HA viscosupplementation(10), it is generally considered as a safe and effective treatment for painful knee OA(11). Despite HA's positive effects, it only provides symptomatic relief and does not restore the affected cartilage to a healthy state. Therefore, other options should be explored.

It is an object of the present invention to provide a solution with lubricating properties that can be used in viscosupplementation, a treatment to increase the lubricating properties of the synovial fluid in arthritic joints of patient suffering from OA.

It was found that the NCM solution has lubricating properties similar to HA solution and is capable of reducing the coefficient of friction (CoF). The reduction of CoF will contribute to a reduction in pain in the joint, thus minimizing the pain and providing relieve for the patient suffering from OA.

The present invention thus provides for the use of an NCM solution in the treatment of osteoarthritis (OA), more particular for use in viscosupplementation in the treatment of OA. Viscosupplementation for the purpose of this invention is understood to be the treatment of OA by intra-articular injection of a lubricant directly in the joint. Preferably, the invention provides for the use of an NCM solution in the treatment of pain in the osteoarthritic joints of a patient suffering from OA. More preferably, the NCM solution is used as a lubricant in the treatment of OA, more specifically in the treatment of pain in the arthritic joints of a patient suffering from OA. The NCM solution can be used as a lubricant in bioactive viscosupllementation in the treatment of OA.

As the NP tissue has no lubricating function, NCM, which is simply composed of NP matrix components, was not expected to act as a boundary or hydrodynamic lubricant.

Further, because lubricin (PRG4), an important glycoprotein bound to the articulating surface of the articular cartilage, was not present in the protein content of NC rich medium, the lubricating properties could not be contributed to the presence of PRG4. It was therefore all the more surprising that an NCM solution could give rise to boundary and hydrodynamic lubrication.

The present invention provides for the use of an NCM solution in a method to treat osteoarthritis (OA), preferably in a method to treat pain in the joints affected by OA. The NCM solution is administered as a lubricant in the joint of a subject suffering from OA to reduce the pain in said joint. The NCM solution preferably is administered by intra-articular injection directly into the joint. The NCM solution is administered in an effective amount so as to achieve a reduction in the cartilage coefficient of friction (CoF) in the affected arthritic joint as compared to the CoF in the non-treated arthritic joint. By reducing the CoF, the pain in the affected arthritic joint will be reduced, thus providing relieve of pain in the patient suffering from OA. The effective amount of NCM solution may vary according to the concentration of the NCM and other factors such as the state of the disease, the age and weight of the patient.

The NCM solutions that are suitable for use as a lubricant can be obtained using general methods of preparation that are common in the art, such as described in WO 2017/121736, de Vries, Stefan et al. (June 2018), supra; Bach F C, et al. (2018), supra; Vries S A H, Doeselaar M, Kaper H J, Sharma P K, Ito K. Notochordal cell matrix as a bioactive lubricant for the osteoarthritic joint. Sci Rep. 2018; 8(1):1-11.; Notochordal cell matrix: An inhibitor of neurite and blood vessel growth? J Orthop Res. 2018; 36(12):3188-3195. A suitable method to prepare the NCM solution comprises the steps of:
- Harvesting notochordal cell (NC)-rich nucleus pulposus (NP) tissue from an intervertebral disc of an animal donor;
- Lyophilizing the NC-rich NP tissue to destroy cells within the tissue, thereby obtaining a dry and brittle NC matrix;
- Pulverizing the dry and brittle matrix to obtain a dry and brittle NC matrix powder; and
- Dissolving the NC matrix powder in a solvent to obtain an NCM solution.

An animal donor according to the invention can be any animal that retains its notochordal cells (NCs) and therefore does not develop degenerative disc disease. These animals therefore maintain their notochordal cells in the NP tissue of the intervertebral disc for many years, even throughout their adult life. Suitable animal donors according to the invention are nonchordodystrophic canines, felines, porcines and the like. Preferably the animal donor is a porcine species, and the intervertebral disc is a porcine intervertebral disc.

Lyophilization can be carried out using standard methods known in the art, such as described for instance in Remington: The Science and Practice of Pharmacy, 21$^{st}$ Edition. Ed David B Troy. Lippincott Williams & Wilkins, Baltimore, 2006. Lyophilization is carried out to destroy and fragment the cells within the NP tissue. A dry and brittle matrix is obtained, which is then pulverized to form a dry and brittle NC matrix powder.

Pulverization of the dry and brittle NC matrix can be carried out using standard methods known in the art and using standard equipment well known in the art. Suitable methods and equipment for pulverization of biologic material are described for instance in de Vries, Stefan et al. (June 2018), supra.

The dry and brittle NC matrix powder is dissolved in a solvent to obtain the NCM solution of the invention. Preferably the solvent is an aqueous solvent, more preferably a buffered aqueous solvent. A suitable aqueous solvents can be any standard aqueous solution that is well known as a pharmaceutically acceptable aqueous carrier solvent such as water, PBS buffer solution, normal saline and the like.

In addition to the lyophilizing-, and pulverizing-step, the tissue may be subjected to a decellularization step to remove cellular and nucleic acid remnants. The animal donating their intervertebral disc may harbour endogenous viruses such as retroviruses in their genome, which could infect human cells. By subjecting the NC matrix to a decellularization step to remove the nucleic acid content, infection by viral nucleic acid can be prevented. Decellularization of the can be carried out using standard decellularization methods well known in the art. Suitable decellularization methods have been described e.g. in WO 2015/048317 and WO 2017/121736. Prior to decellularization, the dry and brittle NC matrix obtained in the lyophilisation step is rehydrated in a solvent, preferably a physiological aqueous solution such as normal saline, PBS solution and the like. Preferably decellularization is carried out by treating the rehydrated NC matrix tissue with a nuclease or detergent or a combination of both. Such treatment result in the substantial removal of nucleic acid content from the NC matrix while maintaining as much of the protein content as possible, as compared to non-decellularized NC matrix. Treatment with the nuclease or detergent or a combination of both results in the removal of at least 80% of the nucleic acids from the NC matrix tissue, as compared to the NP tissue that is not treated. Accordingly, the residual content of nucleic acid is less than 20% in the treated NC matrix, as compared to the untreated matrix.

Suitable nucleases are DNAse, RNAse, Bensonase®, and the like. Suitable detergents are Triton-X® detergents such as Triton-X® 100 and the like. Preferably decellularization is carried out by treatment with Benzonase, more preferably a combination of Benzonase® and Triton-X®-100. The nuclease and detergent remove the nucleic acid in a dose-dependent way. Treatment with nuclease and detergent are well known techniques and the skilled person will be able to determine the dosage and time required using routine skills and his general knowledge. Depending on the dosage and reaction time, any level of nucleic acid removal between 80% and 99% can be achieved. After treatment with the nuclease and/or detergent, the decellularized NC matrix tissue is subjected to several washing steps to remove the nucleic acid remnants. The decellularized NC matrix tissue is then lyophilized again to obtain a dry and brittle NC matrix powder, that can be pulverized and dissolved to obtain a NCM solution according to the invention.

Thus, in a particular aspect, the NCM solutions of the invention can be prepared by a method comprising the steps of:
- Harvesting notochordal cell (NC)-rich notochordal pulposus (NP) tissue from an intervertebral disc of an animal donor;
- Lyophilizing the NC-rich NP tissue to destroy cells within the tissue, thereby obtaining a first dry and brittle matrix;
- Rehydrating the dry and brittle matrix in a solvent and then decellularizing the rehydrated matrixit to remove cellular and nucleic acid remnants;
- Lyophilizing the decellularized matrix to obtain a second dry and brittle matrix;

Pulverizing the second dry and brittle matrix to obtain a dry and brittle NC matrix powder; and Dissolving the NC matrix powder in an aqueous solution to obtain an NCM solution.

The animal donor can be any animal as mentioned before. The lyophilizing-, pulverizing-, and decellularizing- and dissolving steps are carried out as mentioned before.

The NCM solution may comprise additional components such as antibiotics, BSA, hyaluronic acid (HA), or even a sustained release hydrogel.

The NCM solutions of the present invention preferably have a concentration of NC matrix powder in the range of 1-200 mg/ml, preferably 1-100 mg/ml, more preferably 1-50 mg/ml.

The NCM solutions can be used as bioactive lubricant in the treatment of OA, preferably in the treatment of pain in arthritic joints in patients suffering from OA, more preferably in the treatment of OA by viscosupplementation, to minimize the pain in arthritic joints. The joints that can be treated are joints of the knee, elbow, ankle, finger, hip and all other synovial joints that can be affected by OA.

In a further aspect, the NCM solution can be obtained by a method comprising the steps of: method of making a notochordal cell matrix as a bioactive lubricant for an osteoarthritic joint, comprising:

Lyophilizing porcine nucleus pulposus tissue containing notochordal cells to destroy cells within the tissue and to make a dry and brittle tissue;

Treating the dry and brittle tissue to remove cellular and nucleic acid remnants, wherein the treatment results in at least 80% removal of porcine nucleic acids from the porcine nucleus pulposus tissue while substantially maintaining porcine protein content within the porcine nucleus pulposus tissue;

Further lyophilizing the treated material and pulverizing the treated material into a notochordal cell matrix powder; and Solubilizing the notochordal cell matrix powder by dissolving the notochordal cell matrix powder into a solution or a gel.

In a further aspect, the invention provides for a NCM solution for use as a bioactive lubricant. Preferably the bioactive lubricant comprising the NCM solution is obtained with any of the methods described herein. More preferably the bioactive lubricant comprising the NCM solution is obtained from a porcine intervertebral disc using any of the methods described herein.

In one aspect the invention provides for a bioactive lubricant for use in the treatment of OA, wherein the lubricant comprises a solubilized notochordal cell matrix powder. Preferably, the notochordal cell matrix powder originates from lyophilized and treated porcine nucleus pulposus tissue containing notochordal cells, wherein the powder contains less than 20% of porcine nucleic acids, wherein the powder contains a substantially unchanged amount of porcine protein content compared to the originating porcine nucleus pulposus tissue, and wherein the solubilized notochordal cell matrix powder is dissolved in a carrier solvent or formed as a gel.

The invention will be illustrated further by the following examples, without being limited thereto or thereby.

LEGEND OF THE FIGURES

FIG. 1: Porcine NC-rich NP matrix (NCM) induced an anabolic response of bovine chondrocytes (a) Glycosaminoglycan (GAG) and (b) DNA content per alginate bead seeded with bovine chondrocytes, (c) GAG per DNA and (d) hydroxyproline content per bead. Values represent means+ standard deviations, n=5 per group. * indicates $p<0.05$ compared to all other groups, # indicates $p<0.05$ compared to base medium (BM). (e) Alcian blue staining confirms increased GAG deposition with NCM and BM supplemented with 10 ng/ml TGF-$\beta$1 (TGF) compared to BM. Collagen immunohistochemistry shows increased collagen type II at the edge of the bead and more diffuse collagen type II deposition with TGF. Collagen type I staining intensity appears to be increased with NCM.

Figure 2:
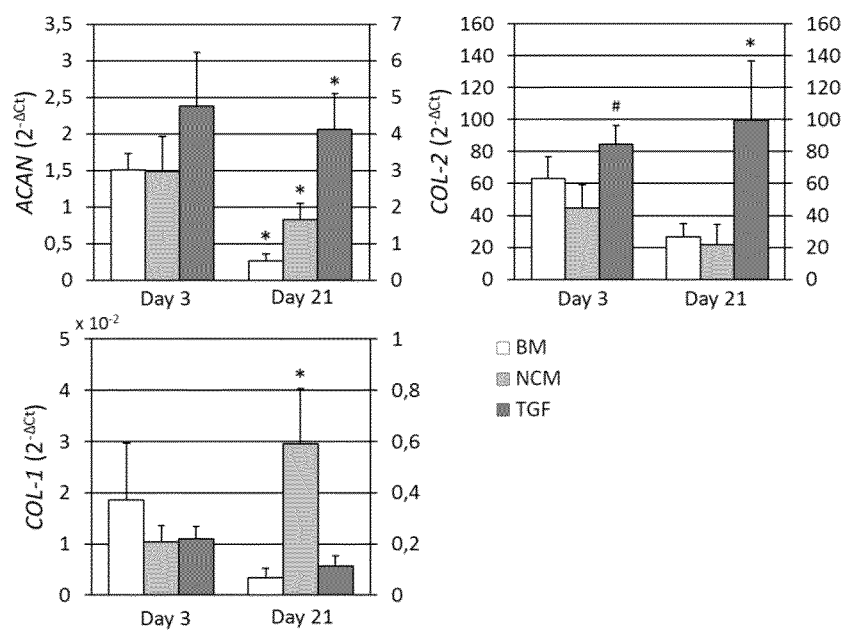

FIG. 2: NC-rich nucleus pulposus matrix (NCM) has distinct anabolic effects in chondrocyte-seeded alginate beads. ACAN: aggrecan; COL-2: collagen type II alpha 1; COL-1: collagen type I alpha 1. Expression levels are relative to 60S ribosomal protein L13 (RPL13). Values are means+standard deviations, n=5 per group. * indicates $p<0.05$ compared to all other groups at the same time point, # indicates $p<0.05$ compared to base medium (BM).

Figure 3:
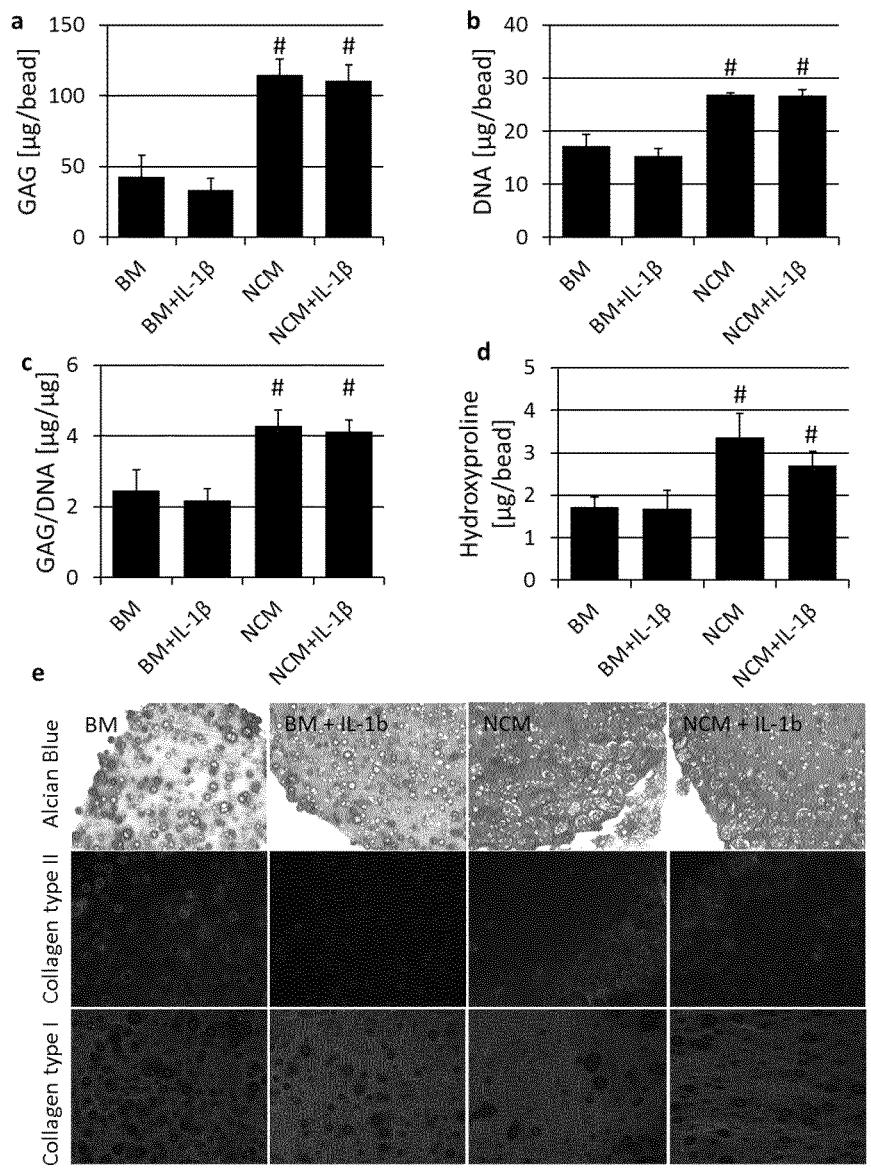

FIG. 3: Addition of an inflammatory stimulus did not affect NCM's regenerative potential (a) Glycosaminoglycan (GAG) and (b) DNA content per alginate bead seeded with bovine chondrocytes, (c) GAG per DNA and (d) hydroxyproline content per bead. Values represent means+standard deviations, n=5 per group. # indicates $p<0.05$ from both base medium (BM) groups. (e) Alcian blue staining confirms increased GAG deposition with both NCM groups compared to both BM groups. Collagen type II staining was less intense with addition of IL-1$\beta$ to BM relative to BM alone which, albeit to a lesser extent, is also observed with addition of IL-1$\beta$ to NCM. Collagen type I deposition appeared to increase with addition of IL-1$\beta$ to BM, though this is not observed with addition of IL-1$\beta$ to NCM.

Figure 4:
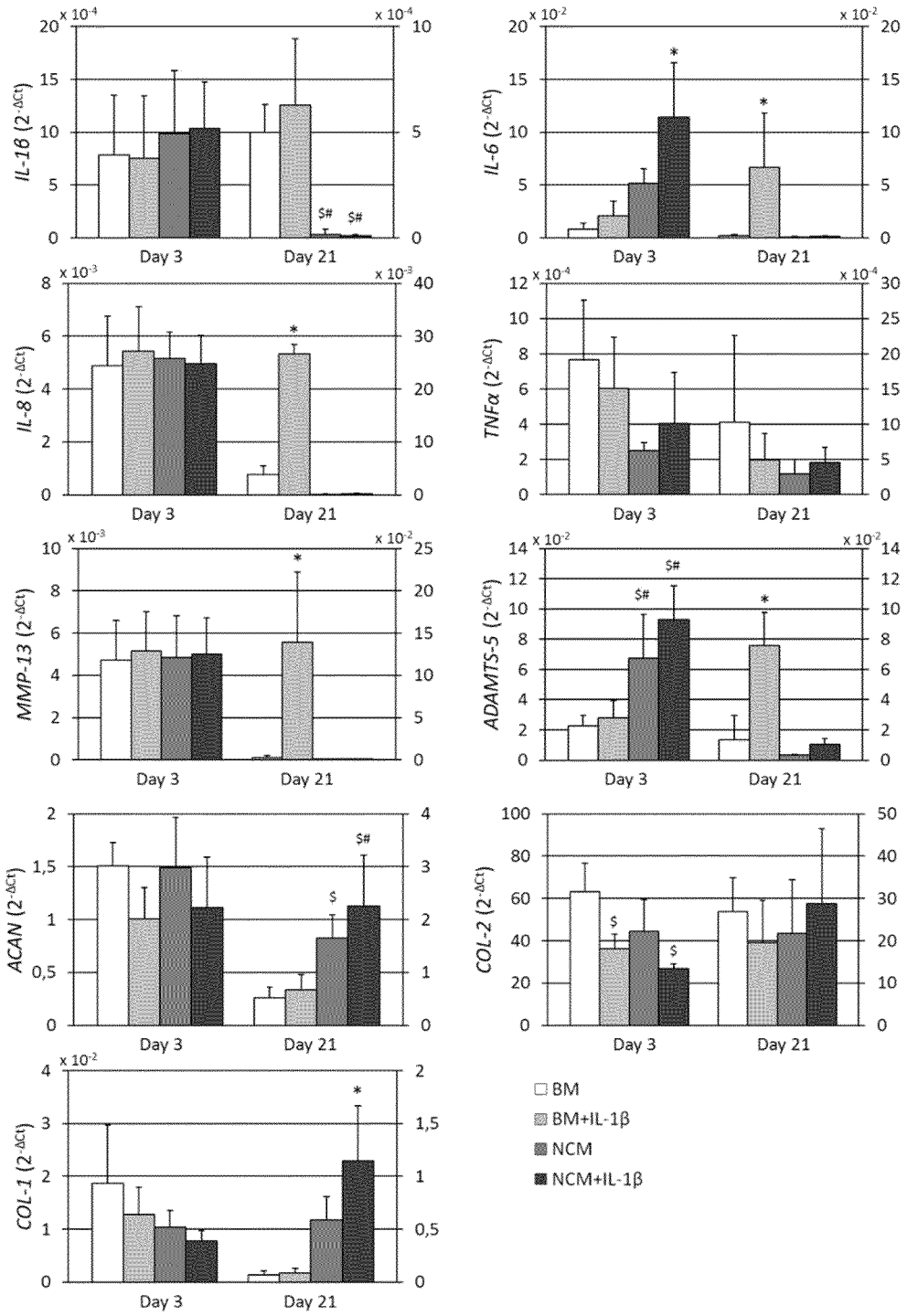

FIG. 4: NC-rich nucleus pulposus matrix (NCM) may have anti-inflammatory and -catabolic potential. IL-1$\beta$/6/8: interleukin-1$\beta$/6/8; TNF$\alpha$: tumor necrosis factor $\alpha$; ADAMTS-5: a disintegrin and metalloproteinase with thrombospondin motifs 5; MMP-13: matrix metalloproteinase 13; ACAN: aggrecan; COL-2: collagen type II alpha 1. COL-1: collagen type I alpha 1. Expression levels are relative to 60S ribosomal protein L13 (RPL13). Values are means+standard deviations, n=4-5 per group. * indicates $p<0.05$ compared to all other groups from the same time point, $ indicates $p<0.05$ compared to base medium (BM), # indicates $p<0.05$ compared to BM+IL-1$\beta$.

Figure 5:
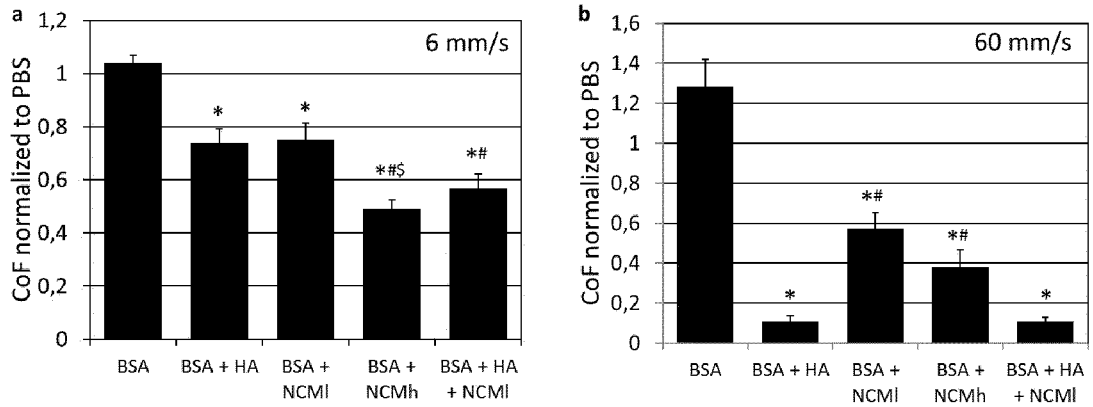

FIG. 5: NC-rich nucleus pulposus matrix (NCM) has potential in cartilage lubrication. Coefficients of friction (COF) at cycle 20 in the different lubricants normalized to COF at cycle 20 in PBS alone at (a) 6 mm/s and (b) 60 mm/s. BSA: 5 mg/ml bovine serum albumin, HA: 4 mg/ml hyaluronic acid, NCMl:4 mg/ml NCM, NCMh: 10 mg/ml NCM. Values are mean+standard error, n=5 for 6 mm/s measurements, n=3 for 60 mm/s measurements. * indicates $p<0.05$ compared to BSA, # indicates $p<0.05$ compared to BSA+HA, $ indicates $p<0.05$ compared to BSA+NCMl.

Figure 6:
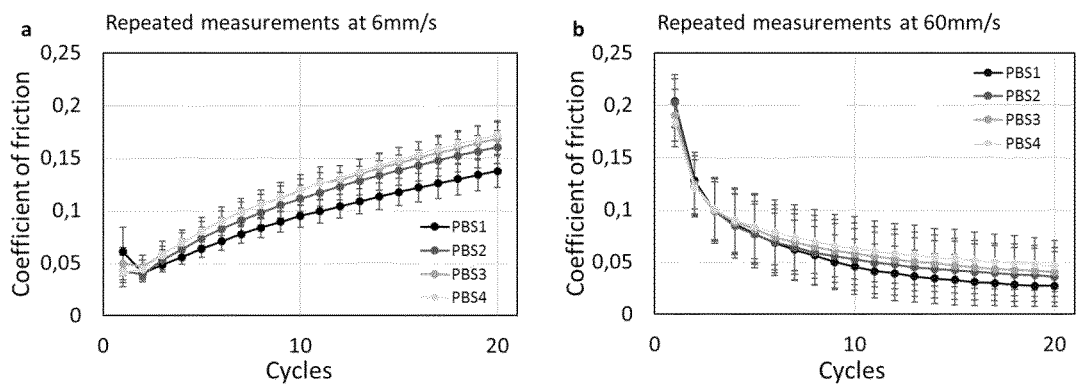

FIG. 6: Repeated rounds of reciprocating sliding of cartilage against glass in PBS do not affect coefficients of friction (CoF). CoF for each cycle of 4 consecutive rounds (PBS1-PBS4, n=4) of cartilage on glass sliding at (a) 6 mm/s and (b) 60 mm/s. Significant differences were observed between multiple rounds of sliding at either of the test speeds for individual measurements.

EXAMPLES

The aim of the current study was to investigate whether it is feasible to use NCM as a biomaterial with lubricating properties, that could simultaneously stimulate chondrocytes to restore the affected cartilage within the OA joint. First, the regenerative potential of NCM on bovine chondrocytes was investigated in an in vitro alginate bead culture. Second, it was investigated whether NCM could also stimulate chondrocytes in the presence of an inflammatory stimulus. Lastly, reciprocating sliding cartilage on glass friction tests were performed to test NCM's lubricating properties relative to and in combination with hyaluronic acid (HA).

Materials and Methods

Production of Porcine NCM

NC-rich NP tissue was harvested from the IVDs of porcine donors (n=5, ~3 months old). The tissue was lyophilized (Labconco, Kansas City, Mo., USA) overnight, resulting in a dry and brittle matrix, which was subsequently pulverized using a microdismembrator (Sartorius, Goettingen, Germany). The NCM powder was aliquoted and stored at −80° C. until further use.

Chondrocyte isolation and alginate bead production

Full-depth slices of articular cartilage where collected from the metacarpal-phalangeal joints of bovine donors (n=5, ~3 years old), and collected in phosphate-buffered saline (PBS) with 15% Penicillin-Streptomycin (P/S). Subsequently, cartilage flakes where incubated for 20 min at 37° C. and 5% $CO_2$ in the presence of 0.1% Amphotericin B. Thereafter, the PBS-P/S-Amphotericin mixture was aspirated and cartilage flakes were digested overnight in digestion medium (hgDMEM supplemented with 10% fetal bovine serum (FBS), 1% P/S, 0.1% Amphotericin B and 0.5% collagenase type II) at 37° C. and 5% $CO_2$. The following day, the cells suspension was strained using a 70 µm cell strainer and chondrocytes were washed twice in fresh hgDMEM. Chondrocytes were resuspended in 1.2% alginate (Sigma, 180947, Zwijndrecht, the Netherlands) at 10 million cells/ml, and alginate beads were produced according to a previous protocol (Guo et al., 1989). Briefly, 10 million cells were mixed with 1 ml alginate using an 18 G mixing needle after which the suspension was aspirated in a syringe. Alginate beads were produced by dropping the cell suspension in a 102 mM calcium chloride (Merck, 102378) solution. Subsequently, beads where washed 3 times with 0.9% sodium chloride (Merck, 106404) solution before being transferred to culture medium.

Alginate Bead Culture

To test NCM's anabolic effect, chondrocyte-seeded alginate beads were cultured in base medium (BM: hgDMEM supplemented with 1% P/S, 1% ITS-1+ (Corning, 354352, Lasne, Belgium), 50 mg/ml ascorbic acid-2-phosphate (Sigma, A8960), 1.25 mg/ml bovine serum albumin (Roche, 10735078001) and 40 mg/ml L-proline (Sigma, P5607)), NCM (2 mg/ml NCM added to BM) or with addition of 10 ng/ml TGF-β1 as a positive control. Furthermore, to test whether NCM has a regenerative effect in an inflammatory environment, alginate beads were also cultured in BM and NCM in the presence of 5 ng/ml IL-1β. Alginate beads were cultured for 3 weeks at 37° C. and 5% $CO_2$ with medium changes twice per week. NCM, TGF-β1 and IL-1β were added with each medium change. After culture, alginate beads were stored at −80° C. for biochemical assays (day 0 and 21) or gene expression analysis (day 3 and 21), or embedded in paraffin for (immuno)histochemical staining (day 28).

Biochemical Content and (Immuno)histochemical Staining

To determine the biochemical content, alginate beads were digested overnight at 60° C. in papain digestion buffer (100 mM phosphate buffer (Sigma, P5244), 5 mM 1-cysteine (Sigma, 200-157-7), 5 mM ethylene diamine tetra-acetic acid (Sigma, 03620), and 140 mg/mL papain (Sigma, P4762). From the digested samples, GAG content was determined with dimethyl-methylene blue (DMMB) assay, modified from a previous protocol18 where shark cartilage chondroitin sulfate (Sigma, C4384) was used as a reference. Hydroxyproline content was measured using the Chloramin-T assay19 with a trans-4-hydroxyproline (Sigma, H54409) reference. DNA content was measured using the Qubit Quantification Platform (Invitrogen).

Paraffin-embedded alginate beads were sectioned and stained with Alcian blue and hematoxylin for visualization of proteoglycan deposition and cell nuclei. For collagen immuno-staining, sections were first dewaxed using xylene and a series of decreasing ethanol concentration. Sections were washed in PBS for 5 minutes and antigen retrieval was performed with citrate buffer for 20 minutes at 96° C. for collagen type I staining, and with 0.05% pepsine in 10 mM HCl for 5 minutes at 37° C. for collagen type II. Samples were washed again twice with PBS with 0.1% tween, and subsequently blocked with 10% normal goat serum for 30 minutes. Samples were then incubated overnight at 4° C. with the primary antibody in 1% NGS in PBS (Abcam, Ab34710, 1:200 dilution for collagen type I and Abcam, Ab180697, 1:200 dilution for collagen type II). The next day, samples were washed twice for 5 minutes in PBS with 0.1% tween, followed by incubation with the secondary antibody (Molecular Probes anti-rabbit IgG, A21428, 1:200 dilution for collagen type I and Molecular Probes anti-mouse IgG2a, A21137, 1:300 dilution for collagen type II) and DAPI (1:500 in PBS). Thereafter, samples were washed again twice in 0.1% tween in PBS and embedded using mowiol. Pictures were taken using a fluorescent microscope (Zeiss Axiovert 200M, Zeiss, Sliedrecht, the Netherlands). Positive control samples (bovine tendon for collagen type I and articular cartilage for collagen type II) were included, as well as negative controls for each sample (i.e. omission of the primary antibody). The negative controls showed no aspecific positive staining.

Gene Expression

Gene expression analysis was performed on 3 alginate beads pooled per group. Alginate beads were dissolved in sodium citrate buffer (55 mM trisodiumcitrate-2-hydrate (Merck, 1064480500), 0.15 M sodium chloride, 25 mM HEPES (Sigma, H3375) in RNAse-free water, pH adjusted to 7.4) for 5 minutes at room temperature. After centrifugation the cell pellet was lysed in 300 µl RLT buffer (Qiagen, 74104, Venlo, The Netherlands) with 1% β-mercapto-ethanol. RNA was extracted and purified using the Qiagen mini-kit (Qiagen, 74104) with an on-column DNAse digestion step. A spectrophotometer (ND-1000, Isogen, de Meern, The Netherlands) was used to test the quantity and purity of isolated RNA. The absence of genomic DNA was verified with a minus-RT reaction (iCycler; Bio-Rad, Veenendaal, The Netherlands). cDNA was synthesized using the VILO-kit (Invitrogen, 11754050). The tested genes and their corresponding primer pairs are listed in Table 1. Ribosomal protein L-13 (RPL-13) was selected as the reference gene as its expression was most stable throughout all culture conditions. Gene expression was investigated using real-time qPCR (CFX384, Bio-Rad) and expression is reported according to the 2-Ct method. In order to be able to make statistical comparisons, Ct values were set to 40 for samples from which no signal was obtained.

TABLE 1

Primer sequences for target and reference genes used in RT-qPCR assays. RPL13: 60S Ribosomal Protein L13; IL-1β/6/8: interleukin-1β/6/8; TNFα: tumor necrosis factor α; ADAMTS-5: a disintegrin and metalloproteinase with thrombospondin motifs 5; MMP-13: matrix metalloproteinase 13; ACAN: aggrecan; COL2A1: collagen type II alpha 1. The annealing temperature of all primer pairs was 60° C.

| Gene | Accession number | Oligonucleotide sequence (5' □ 3') | Product size (bp) |
|---|---|---|---|
| RPL13 | NM 001076998 | FW: CTGCCCCACAAGACCAAG<br>RV: TTGCGAGTAGGCTTCAGAC | 140 |
| IL-1β | NM 174093 | FW: AGCATCCTTTCATTCATCTTTGAAG<br>RV: GGGTGCGTCACACAGAAACTC | 88 |
| IL-6 | NM 173923 | FW: GGGCTCCCATGATTGTGGTA<br>RV: GTGTGCCCAGTGGACAGGTT | 69 |
| IL-8 | NM 173925.2 | FW: TGCTTTTTTGTTTTCGGTTTTTG<br>RV: AACAGGCACTCGGGAATCCT | 71 |
| TNFα | NM 173966 | FW: ACACCATGAGCACCAAAAGC<br>RV: GCAACCAGGAGGAAGGAGAA | 130 |
| ADAMTS-5 | NM 001166515 | FW: TCACTGCCTACTTAGCCCTGAA<br>RV: GCTCCAACCGCTGTAGTTCAT | 125 |
| MMP-13 | NM 174389 | FW: CTTGTTGCTGCCCATGAGTT<br>RV: TTGTCTGGCGTTTTGGGATG | 197 |
| ACAN | NM 173981 | FW: CCAACGAAACCTATGACGTGTACT<br>RV: GCACTCGTTGGCTGCCTC | 107 |
| COL2A1 | NM 001113224 | FW: TGGCTGACCTGACCTGAC<br>RV: GGGCGTTTGACTCACTCC | 187 |
| COL1A1 | NM 174520 | FW: TGAGAGAGGGGTTGTTGGAC<br>RV: AGGTTCACCCTTCACACCTG | 142 |

Preparation of Bovine Osteochondral Plugs

Bovine stifle joints (n=4, 2 years, bulls) where acquired from Kroon Vlees b. v., Groningen, The Netherlands. Excessive skin was removed and the joined was opened, careful not to damage the cartilage surface. A total of 14 osteochondral plugs with a diameter of 12 mm where drilled from the femoral condyles using a hollow drill bit. During drilling, the cartilage was continuously wetted with PBS to prevent overheating of the samples. After removal of the osteochondral plugs from the joint, they were kept in PBS on ice until they were used for tribological tests, within 2 hours.

Tribological Testing

Tribological tests were performed in reciprocating sliding using UMT-3 (Universal Mechanical Tester, Bruker Corporation, USA). A glass surface was fixed in a warmed basin (33° C., the temperature of the knee joint) to allow a film of liquids/lubricants to cover the surface. Osteochondral plugs were mounted on a load cell and slid against the glass surface in a reciprocating configuration. For these tests, the osteochondral plugs were divided in three groups. For group 1 (n=5), the glass surface was first submerged in PBS after which the plug was pressed against the glass until a normal load of 4 N was measured, which will result in a low contact pressure of <0.25 MPa as used in recent studies20. Then reciprocating sliding was performed for 20 cycles (55 mm one-way) at 6 mm/s under a constant normal load, directly followed by 20 cycles at 60 mm/s. Thereafter the plug was unloaded and PBS was aspirated and replaced by PBS with 5 mg/ml bovine serum albumin (PBS+BSA) and the test was repeated. Thereafter, this procedure was also repeated with PBS+BSA with 4 mg/ml hyaluronic acid (PBS+BSA+HA) and with PBS+BSA+HA with 4 mg/ml NCM (PBS+BSA+HA+NCM). For group 2 (n=5) the same test was performed with different medium groups: PBS, PBS+BSA, PBS+BSA with 4 mg/ml NCM (PBS+BSA+NCM1), and PBS+BSA with 10 mg/ml NCM (PBS+BSA+NCMh). During the tests, normal forces and friction forces were monitored, and a custom Matlab script was used to filter the data to incorporate only the data points where the test speed was close to the set speed (a 10% error was allowed), and to calculate the coefficient of friction (CoF). CoFs obtained at the 20th cycle for each measurement were normalized to their respective measurement in PBS alone, to correct for contact area differences. For group 3 (n=4) osteochondral plugs, the same procedure was performed, but each round in fresh PBS to verify that repeated sliding at two speeds did not affect the cartilage surface and thus the measured CoF values.

Statistics

Statistics were performed with Statistical Package for Social Sciences (SPSS, version 22; IBM, Armonk, N.Y.). Normality was tested using the Shapiro-Wilk test. For biochemical and gene expression data, one-way analysis of variance (ANOVA) was performed, followed by independent t-tests post hoc testing with Bonferroni corrections. For gene expression data, a one-way, rather than a two-way ANOVA was performed at each time point, since only differences between medium groups were of interest and not the factor time. For tribological data, normalized CoF values from different lubricant groups were compared with paired (for intra-plug comparisons) or unpaired t-tests (for inter-plug comparisons), in post-hoc fashion with Bonferroni corrections. For PBS control measurements repeated measures ANOVAs were used to compare the CoF values from 4 sequential tests consisting each of 20 cycles at 6 and 60 mm/s.

Result

NCM's Regenerative Potential

Both addition of NCM and TGF resulted in increased GAG content compared to BM (FIG. 1a). Furthermore, GAG content with NCM was significantly higher compared to TGF. A similar pattern is observed with DNA content, which increased with TGF compared to BM, but increased further with NCM (FIG. 1b). These data lead to a similar increased GAG per DNA ratio for NCM and TGF compared to BM (FIG. 1c). Also, hydroxyproline, as a measure for collagen content, increased with both NCM and TGF relative to BM (FIG. 1d). Alcian blue staining confirmed the increased GAG content with NCM and TGF (FIG. 1e). From collagen immunostainings, collagen type II deposition appeared to be stimulated with NCM mainly at the edge of the bead, but especially with TGF compared to BM. Collagen type I deposition appeared not to be affected by TGF, whereas beads cultured in NCM stained more intense.

To determine the anabolic effect of NCM at the gene level, gene expression analysis of ACAN, COL-2 and COL-1 was performed (FIG. 2). At day 3 no differences in ACAN expression was observed between culture groups. At day 21 however, expression of ACAN increased with both NCM and TGF compared to BM, and with TGF compared to NCM. Expression of COL-2 was not significantly different with NCM compared to BM at day 3 and 21, but was significantly higher with TGF compared to NCM at day 3, and compared to BM and NCM at day 21. At day 3 no significant differences in COL-1 expression were observed between culture groups, however COL-1 expression was significantly higher in NCM compared to BM and TGF at day 21.

NCM's Potential in an Inflammatory Environment

To determine whether NCM also has regenerative potential in the presence of an inflammatory stimulus, chondrocyte-seeded alginate beads were cultured in BM and NCM with and without addition of IL-1β. However, addition of IL-1β to BM and NCM did not affect GAG, DNA, GAG per DNA and hydroxyproline content compared to their counterparts without IL-1β (FIG. 3a-d). Alcian blue staining verified the increased GAG content with NCM with and without IL-1β compared to BM with and without IL-1β (FIG. 3e). Interestingly, immunostaining indicated that collagen type II is diminished with addition of IL-1β to BM, whereas this was not as clearly observed with addition of IL-1β to NCM. Furthermore, Addition of IL-1β appeared to increase the production of collagen type I in BM, but not in NCM.

No differences in expression of IL-1β were observed between culture groups at day 3, whereas at day 21 IL-1β expression was significantly lower in both NCM groups compared to both BM groups (FIG. 4). Furthermore, addition of IL-1β did not increase IL-1β expression in either BM or NCM relative to their non-treated control. Expression of IL-6 was significantly higher in NCM with IL-1β compared to all other groups at day 3. However, at day 21 its expression was significantly higher in BM with IL-1β compared to BM alone and both NCM groups. No differences in expression of IL-8 were observed at day 3, whereas its expression was significantly higher in BM with IL-1β compared to all other culture groups. No significant differences between culture groups were observed for TNFα at either day 3 or day 21. At day 3, no significant differences in expression of MMP-13 were observed, but its expression at day 21 was significantly higher in BM with IL-1β compared to BM alone and NCM groups. ADAMTS-5 expression at day 3 was significantly higher in NCM with and without IL-1β compared to both BM groups. However, at day 21 its expression was significantly higher in BM with IL-1β compared to the other groups. No differences in ACAN expression were observed at day 3. At day 21 however, ACAN expression in NCM was significantly higher compared to BM alone, and in NCM with IL-1β it was significantly higher compared to both BM groups. At day 3, addition of IL-1β significantly decreased COL-2 expression compared to BM alone, whereas no significant differences were observed at day 21. No differences were observed for COL-1 expression at day 3, but at day 21 its expression in NCM with IL-1β was significantly higher compared to all other culture groups.

NCM Lubrication

At both 6 and 60 mm/s (FIG. 5a, b) addition of BSA to PBS either made no difference or caused slight increase in CoF. At 6 mm/s, addition of HA and lower amounts of NCM (NCMl) resulted in a significant decrease (by ~27%) in CoF after 20 cycles of sliding, compared to PBS with BSA (FIG. 5a). Combined addition of NCMl and HA resulted in a stronger reduction (45%) in CoF, which was significantly lower compared to BSA alone and BSA with HA, but not compared to BSA with NCMl. The strongest reduction (53%) in CoF was observed with addition of NCMh, where the CoF was significantly lower compared to BSA as well as both BSA with HA and BSA with NCMl.

At 60 mm/s, addition of HA resulted in a 92% decrease in CoF after 20 cycles of sliding, compared to PBS with BSA, addition of HA and NCMl also showed a similar decrease. Addition of NCMl and NCMh respectively caused a significant decrease by 55 and 70% as compared to PBS with BSA (FIG. 5b). To verify that repeated sliding of the same plug did not affect CoF measurements, osteochondral plugs were slid against the glass surface for 4 rounds of 20 cycles, each round in fresh PBS. CoFs did not significantly change at either 6 (FIG. 6a) or 60 mm/s (FIG. 6b) as a result of multiple rounds of sliding. Therefore, no corrections were applied to the data presented in FIGS. 5a and b.

Discussion

NC-secreted factors, applied in the form of conditioned medium, have shown anabolic, proliferative and chondrogenic potential on NPCs and BMSCs12-17. Due to similarities between NPCs and chondrocytes, a translation of NC-secreted factors from IVD applications to the field of chondrocytes/cartilage seems logical. Indeed, NC-conditioned medium recently also demonstrated anabolic and anti-inflammatory effects on human OA chondrocytes. Since direct application of NCM had even stronger anabolic effects on NPCs compared to NC-conditioned medium (de Vries, submitted), it seemed plausible that NCM would have stimulatory effects on chondrocytes as well. Hence, this study tested the feasibility of a novel NCM approach, as a bioactive viscosupplementation lubricant, to minimize joint pain upon injection in the OA joint, while simultaneously providing a regenerative stimulus to the resident chondrocytes.

NCM Exerts Strong Anabolic Effects on Bovine Chondrocytes

Previous findings regarding NC-conditioned medium and NCM are in line with the current results, since NCM exerted strong anabolic effects on bovine chondrocytes as shown by increased GAG, DNA GAG per DNA and hydroxyproline content with NCM compared to BM. NCM resulted in even higher GAG and DNA per bead content compared to addition of 10 ng/ml TGF-β1. However, collagen immunohistochemistry revealed increased deposition of collagen type I with NCM compared to BM and TGF, which is in line with the increased expression of COL-1 with NCM at day 21. Differences in collagen type II deposition between culture groups were less discernible, although collagen type II was consistently present mainly at the edges of the beads with NCM, whereas it was deposited throughout the bead with addition of TGF-β1. This may indicate that TGF-β1 is smaller than the active component(s) of NCM and can diffuse into the bead more easily. As such, it would exert its effects on a higher number of cells, which would explain the higher ACAN and COL-2 gene expression levels observed with TGF-β1 compared to NCM. In line with this, in a previous study where NCM's regenerative potential was tested on NPC-seeded alginate beads, NCM appeared to enhance collagen type II deposition throughout the alginate beads, rather than collagen type I (De Vries, Stefan et al. (June 2018), supra). In that study, NPCs were seeded at a density of 3 million cells/ml, whereas in this study chondrocytes were seeded at 10 million cells/ml, indicating that limited diffusion of NCM's bioactive factors may play a larger role in the current study. Alternatively, it is possible that NPCs and chondrocytes, despite their similarities, respond differently to NCM stimulation in terms of collagen deposition, or that the NPCs used in the previous study where in a healthier state compared to the chondrocytes in the current study. Nonetheless, despite NCM's stimulation of collagen type I rather than type II, it exhibits strong matrix anabolic effects, and further studies are required for a more in-depth characterization of these effects under disease conditions.

NCM has Regenerative Potential in the Presence of an Inflammatory Stimulus

Inflammatory cytokines, which in turn stimulate the release of catabolic factors such as MMPs and ADAMTSs, play a central role in the onset and progression of OA. Therefore, this study tested whether NCM can also elicit a regenerative response of chondrocytes in the presence of an inflammatory stimulus. Gene expression results, mainly at day 21, suggest that addition of IL-1β to BM indeed resulted in an inflammatory environment, as shown by increased IL-6 and IL-8 expression levels. Moreover, IL-1β induced catabolism on the gene level as shown by increased MMP-13 and ADAMTS-5 expression levels at day 21 in BM. However, treatment of the NCM group with IL-1β did not result in increased expression levels of these genes relative to BM or NCM alone, suggesting that NCM has anti-inflammatory and -catabolic potential, as also observed in previous in vitro and in vivo studies testing the effects of NCM on NPCs (de Vries, Stefan et al(June 2018), supra; Bach F C et al., (2018), supra.). Interestingly IL-1β and INFα did not respond to addition of IL-1β to either BM or NCM, which is not in line with previous findings(21). This may be due to species and/or age differences, as the previous experiment used chondrocytes obtained from relatively older age human donors, which are likely more sensitive to an inflammatory stimulus. Nonetheless, IL-1β gene expression was significantly lower in both NCM groups relative to both BM groups, which underscores NCM's anti-inflammatory potential.

The inflammatory stimulus applied during culture did not significantly affect GAG, DNA and hydroxyproline content, indicating that NCM's anabolic and proliferative effects are maintained in an inflammatory environment. This is also verified by ACAN gene expression levels, which were not significantly different in NCM treated with IL-1β compared to NCM alone. However, NCM in combination with IL-1β seemed to further induce unfavourable collagen production, as observed by decreased collagen type II staining intensity and COL-2 gene expression at day 3, and increased COL-1 gene expression at day 21 for NCM treated with IL-1β. At day 21 however, no significant differences in COL-2 expression levels were observed, which suggests that collagen type II production has recovered over the culture time, despite the continuous presence of IL-1β. Furthermore, a supra-physiological concentration of IL-1β was applied, and NCM's potential in an inflammatory environment should be further investigated in a more physiological setting, e.g. in vivo.

NCM has Cartilage Lubricating Properties

In addition to its regenerative effects on chondrocytes, this study shows that low concentrations (4 and 10 mg/ml) of NCM solutions were capable of reducing cartilage CoF. Thus NCM may be applied as an OA joint lubricant with or without HA.

Tribological control measurements (i.e. 4 repeated rounds of reciprocating sliding of the same osteochondral plug, each time in fresh PBS) demonstrated that there were no significant differences between runs, and thus no corrections were applied to the other experiments. This strategy of using the same plug repeatedly is thus successful in avoiding differences in contact area due to joint to joint biological variations in cartilage properties.

At both 6 and 60 mm/s, addition of BSA to PBS either made no difference or caused slight increase in CoF. This was not unexpected. BSA is a non-glycosylated globular protein and was not expected to either provide boundary or hydrodynamic lubrication. Moreover, albumin has been implicated in interfering with lubricin (PRG4) adsorption on natural cartilage(22) and biomaterial(23) surfaces. BSA is an abundant synovial fluid protein thus it's effect was necessary to monitor in our measurements (all lubricant solutions contained 5 mg/ml BSA except PBS controls).

At low speeds, e.g. 6 mm/s, neither hydrodynamic(6, 7) nor tribohydration20 mechanisms of cartilage lubrication are expected to apply. At this speed in natural cartilage, adsorbed molecules on the cartilage surface provide boundary lubrication. Lubricin (PRG4) is an important glycoprotein bound to the articulating surface of AC, i.e. the lamina splendens. It is anchored in a looped or one-end-free fashion providing boundary lubrication. In addition to PRG4, surface active phospholipids (SAPL) belong to the most researched boundary lubricants24-26. As the NP tissue has no lubricating function, NCM, which is simply composed of NP matrix components, was not expected to act as a boundary lubricant. In a previous study investigating the proteomic contents of porcine NC-conditioned medium, PRG4 was not shown to be present27. Also notochordal cell vacuoles are speculated to contain lipids28, but their surface-activity has never reported on. Finally, the mucopolysaccharides present in the NC matrix may also be surface active and give rise to boundary lubrication. However, past studies reported that concentrations as high as 100 mg/ml of chondroitin sulfate was necessary to decrease the coefficient of friction29 whereas in this study the concentration of NCM used would have resulted in only 1.5 and 4 mg/ml of GAGs. Thus, it was surprising that boundary lubrication was NCM's stronger mode of action, i.e. more than at higher speeds, and some component other than PRG4 would be providing boundary lubrication to the cartilage at these lower speeds. The fact that addition of NCM induced a dose-dependent decrease in CoF would be consistent with its boundary lubricant mechanism. At 4 mg/ml, this effect was similar to HA at a concentration similar to that used clinically for viscosupplementation. Finally, when added to HA, it further decreased the CoF indicating absence of any antagonistic interaction between HA and NCM and perhaps a differing mode of action.

At higher speeds e.g. 60 mm/s, hydrodynamic lubrication, where a wedge of fluid is created when opposing cartilage surfaces slide on each other6, 7, 30, comes into play, and furthermore, tribohydration(20) will become active. This type of lubrication depends, among others, on the viscosity of the trapped fluid. As NCM is rich in mucopolysaccharides27, it might be expected to have some lubricating effects in this fashion. However, during the experiments, it was visually observed that a 4 mg/ml HA solution was more viscous compared to NCMl(4 mg/ml) and even NCMh (10 mg/ml) solutions, and it was doubtful that NCM would be effective. Nevertheless, NCM had a lubricating effect at this test speed, as it reduced the CoF ~55% at 4 mg/ml and ~70% at 10 mg/ml relative to PBS+BSA, even though this was less of a decrease in CoF then that with HA. This could suggest that the lubricating mechanism of NCM at higher speeds may not purely be through its viscosity but also due to other unknown effects. Again, at this speed, the combination of NCMl with HA induced a similar reduction in CoF to HA alone, indicating no antagonism and that this combination may ultimately be applied clinically in order to maximize the lubricating properties while still benefitting from NCM's regenerative potential.

Conclusions

In conclusion, this study demonstrates that NCM exerts regenerative effects on bovine chondrocytes, and has strong lubricating properties on articular cartilage. Therefore, NCM holds promise as a therapy for OA, where it may be applied to minimize pain directly upon injection into the joint, while simultaneously inducing a regenerative stimulus to the resident chondrocytes, that may restore the affected cartilage tissue towards a healthy state. Further studies should focus on NCM's regenerative effects in a more physiological model, and on processing methods for the clinical application of NCM.

REFERENCES

1. Lawrence R C, Felson D T, Helmick C G, et al. Estimates of the Prevalence of Arthritis and Other Rheumatic Conditions in the United States Part II. *Arthritis Rheum.* 2008; 58(1):26-35. doi:10.1002/art.23176.
2. Porcheret M, Jordan K, Jinks C, Croft P. Primary care treatment of knee pain—A survey in older adults. *Rheumatology.* 2007; 46(11):1694-1700. doi:10.1093/rheumatology/kem232.
3. Altman R D, Manjoo A, Fierlinger A, Niazi F, Nicholls M. The mechanism of action for hyaluronic acid treatment in the osteoarthritic knee: A systematic review. *BMC Musculoskelet Disord.* 2015; 16:321-331. doi:10.1186/s12891-015-0775-z.
4. Balazs E A. The Physical Properties of Synovial Fluid and the Special Role of Hyaluronic Acid. *Disord Knee.* 1974; 5:63-75.
5. Goldberg V M, Buckwalter J A. Hyaluronans in the treatment of osteoarthritis of the knee: Evidence for disease-modifying activity. *Osteoarthr Cartil.* 2005; 13(3):216-224. doi:10.1016/j.joca.2004.11.010.
6. Greene G W, Banquy X, Lee D W, Lowrey D D, Yu J, Israelachvili J N. Adaptive mechanically controlled lubrication mechanism found in articular joints. *Proc Natl Acad Sci.* 2011; 108(13):5255-5259. doi:10.1073/pnas.1101002108.
7. Greene G W, Banquy X, Lee D W, Lowrey D D, Yu J, Israelachvili J N. Reply to McCutchen: Clarification of hydrodynamic and boundary lubrication mechanisms in joints. *Proc Natl Acad Sci.* 2011; 108(33):E462-E462. doi:10.1073/pnas.1107412108.
8. Jahn S, Seror J, Klein J. Lubrication of Articular Cartilage. *Annu Rev Biomed Eng.* 2016; 18:235-258. doi:10.1146/annurev-bioeng-081514-123305.
9. Kogan G, Šoltés L, Stern R, Gemeiner P. Hyaluronic acid: A natural biopolymer with a broad range of biomedical and industrial applications. *Biotechnol Lett.* 2007; 29:17-25. doi:10.1007/s10529-006-9219-z.
10. Bannuru R R, Vaysbrot E E, Sullivan M C, McAlindon T E. Relative efficacy of hyaluronic acid in comparison with NSAIDs for knee osteoarthritis: A systematic review and meta-analysis. *Semin Arthritis Rheum.* 2014; 43:593-599. doi:10.1016/j.semarthrit.2013.10.002.
11. Henrotin Y, Raman R, Richette P, et al. Consensus statement on viscosupplementation with hyaluronic acid for the management of osteoarthritis. *Semin Arthritis Rheum.* 2015; 45:140-149. doi:10.1016/j.semarthrit.2015.04.011.
12. de Vries S A H, Potier E, van Doeselaar M, Meij B P, Tryfonidou M A, Ito K. Conditioned Medium Derived from Notochordal Cell-Rich Nucleus Pulposus Tissue Stimulates Matrix Production by Canine Nucleus Pulposus Cells and Bone Marrow-Derived Stromal Cells. *Tissue Eng Part A.* 2015; 21(5-6):1077-1084. doi:10.1089/ten.tea.2014.0309.
13. Bach F C, de Vries S A H, Krouwels A, et al. The species-specific regenerative effects of notochordal cell-conditioned medium on chondrocyte-like cells derived from degenerated human intervertebral discs. *Eur Cell Mater.* 2015; 30:132-137.
14. Potier E, de Vries S, van Doeselaar M, Ito K. Potential application of notochordal cells for intervertebral disc regeneration: An in vitro assessment. *Eur Cells Mater.* 2014; 28.
15. Abbott R D, Purmessur D, Monsey R D, Iatridis J C. Regenerative potential of TGFβ3+Dex and notochordal cell conditioned media on degenerated human intervertebral disc cells. *J Orthop Res.* 2012; 30(3):482-488. doi:10.1002/jor.21534.
16. Korecki C L, Taboas J M, Tuan R S, Iatridis J C. Notochordal cell conditioned medium stimulates mesenchymal stem cell differentiation toward a young nucleus pulposus phenotype. *Stem Cell Res Ther.* 2010; 1(2):18. doi:10.1186/scrt18.
17. Purmessur D, Schek R M, Abbott R D, Ballif B A, Godburn K E, Iatridis J C. Notochordal conditioned media from tissue increases proteoglycan accumulation and promotes a healthy nucleus pulposus phenotype in human mesenchymal stem cells. *Arthritis Res Ther.* 2011; 13:81-93. doi:10.1186/ar3344.
18. Farndale R W, Sayers C A, Barrett A J. A direct spectrophotometric microassay for sulfated glycosaminoglycans in cartilage cultures. *Connect Tissue Res.* 1982; 9(4):247-248.
19. Huszar G, Maiocco J, Naftolin F. Monitoring of collagen and collagen fragments in chromatography of protein mixtures. *Anal Biochem.* 1980; 105:424-429. doi:10.1016/0003-2697(80)90481-9.

20. Moore A C, Burris D L. Tribological rehydration of cartilage and its potential role in preserving joint health. *Osteoarthr Cartil.* 2016; (September). doi:10.1016/j.joca.2016.09.018.
21. Sandell L J, Xing X, Franz C, Davies S, Chang L W, Patra D. Exuberant expression of chemokine genes by adult human articular chondrocytes in response to IL-1β. *Osteoarthr Cartil.* 2008; 16(12):1560-1571. doi:10.1016/j.joca.2008.04.027.
22. Majd S E, Kuijer R, Köwitsch A, Groth T, Schmidt T A, Sharma P K. Both hyaluronan and collagen type II keep proteoglycan 4 (lubricin) at the cartilage surface in a condition that provides low friction during boundary lubrication. *Langmuir.* 2014; 30:14566-14572. doi:10.1021/la504345c.
23. Majd S E, Kuijer R, Schmidt T A, Sharma P K. Role of hydrophobicity on the adsorption of synovial fluid proteins and biolubrication of polycarbonate urethanes: Materials for permanent meniscus implants. *Mater Des.* 2015; 83. doi:10.1016/j.matdes.2015.06.075.
24. Seror J, Zhu L, Goldberg R, Day A J, Klein J. Supramolecular synergy in the boundary lubrication of synovial joints. *Nat Commun.* 2015; 6:6497. doi:10.1038/ncomms7497.
25. McNary S M, Athanasiou K A, Reddi A H. Engineering Lubrication in Articular Cartilage. *Tissue Eng Part B Rev.* 2012; 18(2):88-100. doi:10.1089/ten.teb.2011.0394.
26. Schmidt T A, Gastelum N S, Nguyen Q T, Schumacher B L, Sah R L. Boundary lubrication of articular cartilage: Role of synovial fluid constituents. *Arthritis Rheum.* 2007; 56(3):882-891. doi:10.1002/art.22446.
27. Bach F C, de Vries S A H, Riemers F M, et al. Soluble and pelletable factors in porcine, canine and human notochordal cell-conditioned medium: Implications for IVD regeneration. *Eur Cells Mater.* 2016; 32. doi:10.22203/eCM.v032a11.
28. Hunter C J, Matyas J R, Duncan N a. The three-dimensional architecture of the notochordal nucleus pulposus: novel observations on cell structures in the canine intervertebral disc. *J Anat.* 2003; 202:279-291. doi:10.1046/j.1469-7580.2003.00162.x.
29. Basalo I M, Chahine N O, Kaplun M, Chen F H, Hung C T, Ateshian G A. Chondroitin sulfate reduces the friction coefficient of articular cartilage. *J Biomech.* 2007; 40:1847-1854. doi:10.1016/j.jbiomech.2006.07.007.
30. Singh N. Synovial Joints and Lubrication mechanisms. *Int J Comput Appl Math.* 2017; 12(1):29-33.

The invention claimed is:

1. A method for treating osteoarthritis (OA) in a synovial joint comprising administering a notochordal cell matrix (NCM) solution into an osteoarthritic (OA) synovial joint of a patient suffering from OA.

2. The method according to claim 1, wherein the NCM solution is administered to treat pain in the OA synovial joint.

3. The method according to claim 1, wherein the NCM solution is used as a lubricant.

4. The method according to claim 1, wherein the NCM solution is used as a bioactive lubricant in viscosupplementation.

5. The method according to claim 1, wherein the solution is an aqueous solution.

6. The method according to claim 1, wherein the NCM solution is obtained by a method comprising:
   harvesting notochordal cell (NC)-rich nucleus pulposus (NP) tissue from an intervertebral disc of an animal donor;
   lyophilizing the NC-rich NP tissue to destroy cells within the tissue, thereby obtaining a dry and brittle matrix;
   pulverizing the dry and brittle matrix to obtain a dry and brittle NC matrix powder; and
   dissolving the NC matrix powder in an aqueous solution to obtain the NCM solution.

7. The method according to claim 1, wherein the NCM solution is obtained by a method comprising:
   harvesting notochordal cell (NC)-rich nucleus pulposus (NP) tissue from an intervertebral disc of an animal donor;
   lyophilizing the NC-rich NP tissue to destroy cells within the tissue, thereby obtaining a first dry and brittle matrix;
   rehydrating the dry and brittle matrix in a solvent and decellularizing the rehydrated matrix to remove cellular and nucleic acid remnants;
   lyophilizing the decellularized matrix to obtain a second dry and brittle matrix;
   pulverizing the second dry and brittle matrix to obtain a dry and brittle NC matrix powder; and
   dissolving the NC matrix powder in an aqueous solution to obtain the NCM solution.

8. The method according to claim 1, wherein the NCM solution is obtained from the intervertebral disc of a porcine donor.

9. The method according to claim 1, wherein the NCM solution is administered by intra-articular injection.

10. The method according to claim 1, wherein the administration of the NCM solution restores affected cartilage tissue in the OA synovial joint.

11. The method according to claim 1, wherein a concentration of NCM powder in the NCM solution is in a range of from 1 to 200 mg/ml.

12. The method according to claim 1, wherein the NCM solution is capable of stimulating cell proliferation and an increase in glycosaminoglycans.

13. A method of treating an osteoarthritic (OA) synovial joint, comprising administering a lubricant to the OA synovial joint to treat the OA synovial joint, wherein the lubricant includes a notochordal cell matrix (NCM) solution.

14. The method according to claim 13, wherein the lubricant is administered by intra-articular injection.

15. The method according to claim 13, wherein a concentration of NCM powder in the NCM solution is in a range of from 1 to 200 mg/ml.

16. The method according to claim 13, wherein the NCM solution further comprises hyaluronic acid (HA).

17. The method according to claim 13, wherein the NCM solution is prepared by a method comprising:
- lyophilizing porcine nucleus pulposus tissue containing notochordal cells to destroy cells within the tissue and to make a dry and brittle tissue;
- treating the dry and brittle tissue to remove cellular and nucleic acid remnants, wherein the treatment results in at least 80% removal of porcine nucleic acids from the porcine nucleus pulposus tissue while maintaining porcine protein content within the porcine nucleus pulposus tissue;
- lyophilizing the treated material and pulverizing the treated material into a notochordal cell matrix powder; and
- solubilizing the notochordal cell matrix powder by dissolving the notochordal cell matrix powder into a solution or a gel.

18. The method according to claim 13, wherein the NCM solution is capable of stimulating cell proliferation and an increase in glycosaminoglycans.

19. The method according to claim 1, wherein the OA synovial joint is selected from the group consisting of: a knee, elbow, ankle, finger, and hip of the patient suffering from OA.

20. The method according to claim 13, wherein the OA synovial joint is selected from the group consisting of: a knee, elbow, ankle, finger, and hip of a patient suffering from OA.

* * * * *

SEQUENCE LISTING

```
<160> NUMBER OF SEQ ID NOS: 20

<210> SEQ ID NO 1
<211> LENGTH: 18
<212> TYPE: DNA
<213> ORGANISM: artificial sequence
<220> FEATURE:
<223> OTHER INFORMATION: synthetic primer sequence

<400> SEQUENCE: 1
ctgccccaca agaccaag                                                     18

<210> SEQ ID NO 2
<211> LENGTH: 19
<212> TYPE: DNA
<213> ORGANISM: artificial sequence
<220> FEATURE:
<223> OTHER INFORMATION: synthetic primer sequence

<400> SEQUENCE: 2
ttgcgagtag gcttcagac                                                    19

<210> SEQ ID NO 3
<211> LENGTH: 25
<212> TYPE: DNA
<213> ORGANISM: artificial sequence
<220> FEATURE:
<223> OTHER INFORMATION: synthetic primer sequence

<400> SEQUENCE: 3
agcatccttt cattcatctt tgaag                                             25

<210> SEQ ID NO 4
<211> LENGTH: 21
<212> TYPE: DNA
<213> ORGANISM: artificial sequence
<220> FEATURE:
<223> OTHER INFORMATION: synthetic primer sequence

<400> SEQUENCE: 4
```
gggtgcgtca cacagaaact c                                               21

<210> SEQ ID NO 5
<211> LENGTH: 20
<212> TYPE: DNA
<213> ORGANISM: artificial sequence
<220> FEATURE:
<223> OTHER INFORMATION: synthetic primer sequence

<400> SEQUENCE: 5
gggctcccat gattgtggta                                                 20

<210> SEQ ID NO 6
<211> LENGTH: 20
<212> TYPE: DNA
<213> ORGANISM: artificial sequence
<220> FEATURE:
<223> OTHER INFORMATION: synthetic primer sequence

<400> SEQUENCE: 6
gtgtgcccag tggacaggtt                                                 20

<210> SEQ ID NO 7
<211> LENGTH: 23
<212> TYPE: DNA
<213> ORGANISM: artificial sequence
<220> FEATURE:
<223> OTHER INFORMATION: synthetic primer sequence

<400> SEQUENCE: 7 tgctttttg ttttcggttt ttg                                              23

<210> SEQ ID NO 8
<211> LENGTH: 20
<212> TYPE: DNA
<213> ORGANISM: artificial sequence
<220> FEATURE:
<223> OTHER INFORMATION: synthetic primer sequence

<400> SEQUENCE: 8
aacaggcact cgggaatcct                                                 20

<210> SEQ ID NO 9
<211> LENGTH: 20
<212> TYPE: DNA
<213> ORGANISM: artificial sequence
<220> FEATURE:
<223> OTHER INFORMATION: synthetic primer sequence

<400> SEQUENCE: 9
acaccatgag caccaaaagc                                                 20

<210> SEQ ID NO 10
<211> LENGTH: 20
<212> TYPE: DNA
<213> ORGANISM: artificial sequence
<220> FEATURE:
<223> OTHER INFORMATION: synthetic primer sequence

<400> SEQUENCE: 10
gcaaccagga ggaaggagaa                                                 20

<210> SEQ ID NO 11
<211> LENGTH: 22
<212> TYPE: DNA
<213> ORGANISM: artificial sequence

```
<220> FEATURE:
<223> OTHER INFORMATION: synthetic primer sequence

<400> SEQUENCE: 11
tcactgccta cttagccctg aa                                              22

<210> SEQ ID NO 12
<211> LENGTH: 21
<212> TYPE: DNA
<213> ORGANISM: artificial sequence
<220> FEATURE:
<223> OTHER INFORMATION: synthetic primer sequence

<400> SEQUENCE: 12
gctccaaccg ctgtagttca t                                               21

<210> SEQ ID NO 13
<211> LENGTH: 20
<212> TYPE: DNA
<213> ORGANISM: artificial sequence
<220> FEATURE:
<223> OTHER INFORMATION: synthetic primer sequence

<400> SEQUENCE: 13
cttgttgctg cccatgagtt                                                 20

<210> SEQ ID NO 14
<211> LENGTH: 20
<212> TYPE: DNA
<213> ORGANISM: artificial sequence
<220> FEATURE:
<223> OTHER INFORMATION: synthetic primer sequence

<400> SEQUENCE: 14
ttgtctggcg ttttgggatg                                                 20

<210> SEQ ID NO 15
<211> LENGTH: 24
<212> TYPE: DNA
<213> ORGANISM: artificial sequence
<220> FEATURE:
<223> OTHER INFORMATION: synthetic primer sequence

<400> SEQUENCE: 15
ccaacgaaac ctatgacgtg tact                                            24

<210> SEQ ID NO 16
<211> LENGTH: 18
<212> TYPE: DNA
<213> ORGANISM: artificial sequence
<220> FEATURE:
<223> OTHER INFORMATION: synthetic primer sequence

<400> SEQUENCE: 16
gcactcgttg gctgcctc                                                   18

<210> SEQ ID NO 17
<211> LENGTH: 18
<212> TYPE: DNA
<213> ORGANISM: artificial sequence
<220> FEATURE:
<223> OTHER INFORMATION: synthetic primer sequence

<400> SEQUENCE: 17
tggctgacct gacctgac                                                   18
```

```
<210> SEQ ID NO 18
<211> LENGTH: 18
<212> TYPE: DNA
<213> ORGANISM: artificial sequence
<220> FEATURE:
<223> OTHER INFORMATION: synthetic primer sequence

<400> SEQUENCE: 18
gggcgtttga ctcactcc                                                   18

<210> SEQ ID NO 19
<211> LENGTH: 20
<212> TYPE: DNA
<213> ORGANISM: artificial sequence
<220> FEATURE:
<223> OTHER INFORMATION: synthetic primer sequence

<400> SEQUENCE: 19
tgagagaggg gttgttggac                                                 20

<210> SEQ ID NO 20
<211> LENGTH: 20
<212> TYPE: DNA
<213> ORGANISM: artificial sequence
<220> FEATURE:
<223> OTHER INFORMATION: synthetic primer sequence

<400> SEQUENCE: 20
aggttcaccc ttcacacctg                                                 20
```